United States Patent [19]

Hall et al.

[11] 4,308,410
[45] Dec. 29, 1981

[54] PRODUCTION OF CHLOROPRENE

[75] Inventors: Antony H. P. Hall, Sutton, England; Jean P. Merle, Echirolles, France

[73] Assignees: BP Chemicals Limited, London, England; Distugil S.A., Cedex, France

[21] Appl. No.: 905,161

[22] Filed: May 12, 1978

Related U.S. Application Data

[63] Continuation of Ser. No. 769,697, Feb. 17, 1977, abandoned.

[30] Foreign Application Priority Data

Feb. 19, 1976 [GB] United Kingdom ................. 6552/76

[51] Int. Cl.$^3$ .............................................. C07C 17/34
[52] U.S. Cl. .................................................. 570/229
[58] Field of Search ......................... 260/655; 570/229

[56] References Cited

U.S. PATENT DOCUMENTS

| 2,999,888 | 9/1961 | Crocker et al. | 260/655 |
|---|---|---|---|
| 3,026,360 | 3/1962 | Lachowicz | 260/655 |
| 3,965,203 | 6/1976 | Smith, Jr. | 260/655 |
| 3,978,146 | 8/1976 | Ohorodnik et al. | 260/655 |
| 3,981,937 | 9/1976 | Campbell et al. | 260/655 |

FOREIGN PATENT DOCUMENTS

| 1814075 | 12/1968 | Fed. Rep. of Germany | 260/655 |
|---|---|---|---|
| 42-25054 | 7/1967 | Japan | 260/655 |

*Primary Examiner*—Delbert E. Gantz
*Assistant Examiner*—Joseph A. Boska
*Attorney, Agent, or Firm*—Brooks, Haidt, Haffner & Delahunty

[57] ABSTRACT

Chloroprene is produced by continuous dehydrochlorinating 3,4-dichlorobutene- 1 at 40°–70° C. in two phase liquid mixture of water and alcohol with standing alkali metal hydroxide of not more than 10% by weight in aqueous phase and separating an organic liquid phase containing chloroprene from the resulting mixture.

13 Claims, 1 Drawing Figure

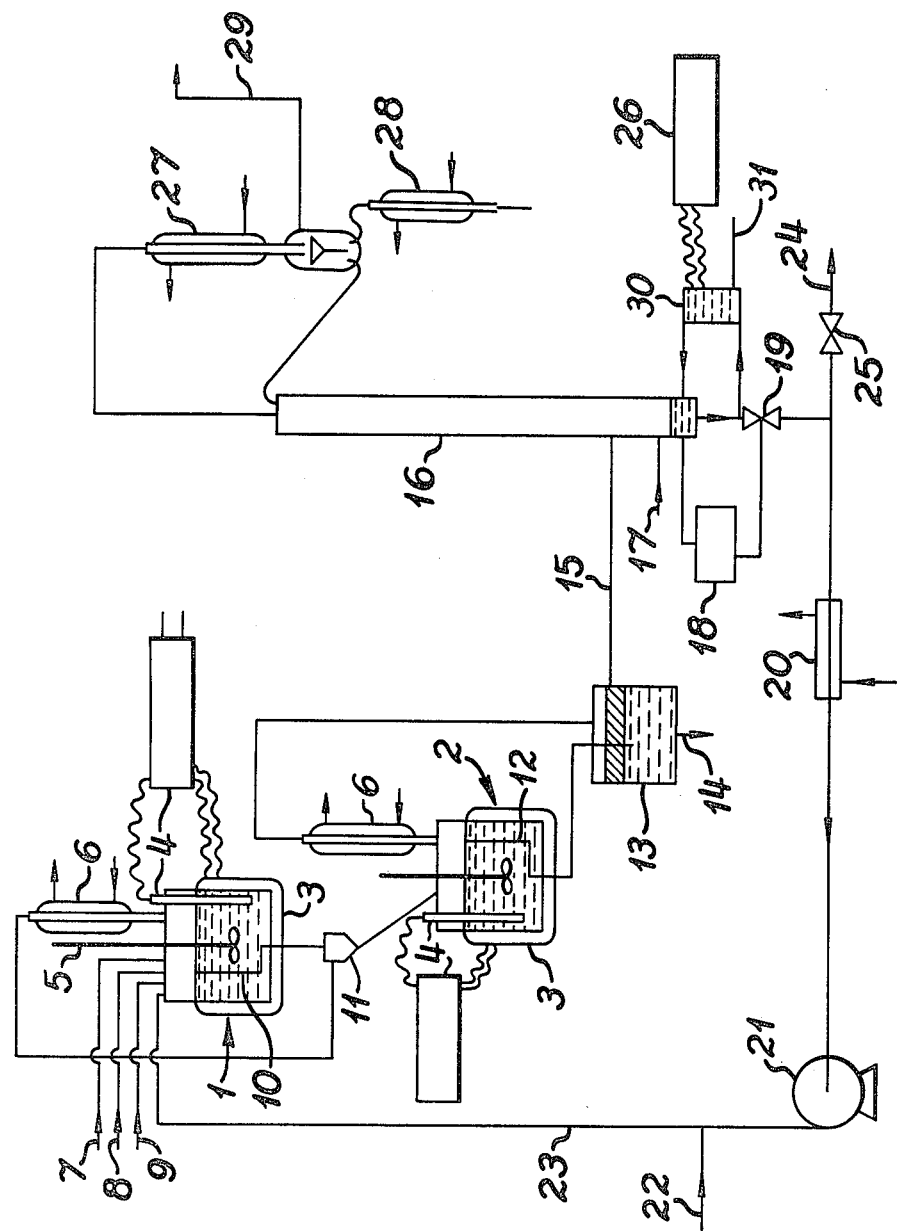

PRODUCTION OF CHLOROPRENE

This is a continuation of application Ser. No. 469,697 filed Feb. 17, 1977 now abandoned.

The present invention relates to the dehydrochlorination of 3,4-dichlorobutene-1 to give chloroprene (2-chloro-butadiene).

U.S. Pat. No. 2,322,258 discloses dehydrochlorination of halogenated organic compounds to form for example mono-, di-, or trichloro-ethylene using alkali metal hydroxides in the presence of hydroxyethers. These hydroxyethers are said to be catalysts and the specification suggests that very small amounts of these catalysts can be used. Water may be present but is preferably absent. The specification refers to the use of temperatures in the range 50° C. and 150° C. but indicates that in most cases the unsaturated organic product will be distilled off as it is formed. No mention is made of the production of chloroprene.

In the case of the production of chloroprene by dehydrochlorination, the distillation of the chloroprene from the reaction mixture as it is formed has been the usual commercial practice.

Thus the production of chloroprene by dehydrochlorination of 3,4-dichlorobutene-1 using aqueous sodium hydroxide is well-known and is currently used for the commercial production of chloroprene. In order to obtain high reaction rates and at the same time to avoid prolonged contact between the chloroprene and the dehydrochlorination reaction mixture it has been preferred to operate the dehydrochlorination step at a temperature such that the chloroprene distills off as it is formed at the reaction pressure, which is most conveniently close to atmospheric pressure.

The apparent desirability of distilling off chloroprene as it is formed, even in systems which are not simple aqueous dehydrochlorinations, is illustrated by U.S. Pat. No. 3,079,446, which discloses the dehydrochlorination of 3,4-dichlorobutene-1 to give chloroprene in the presence of water and certain organic solvents including ether-alcohols. The specification states that the process is carried out at temperatures in the range 80° C. to 120° C., i.e. above the boiling point of chloroprene at atmospheric pressure. Furthermore the chloroprene was distilled off as it was formed in all the Examples in which satisfactory results were obtained. The desirability of using relatively high reaction temperatures and distilling off the chloroprene as it is formed is further illustrated by German Pat. No. 2 503 826. The importance of having little time for reaction of the chloroprene before it is distilled from the reaction mixture is also stressed in this German specification, which also states that temperatures from about 75° C. to 125° C. are used.

British Pat. No. 1,197,539 discloses a process in which quite low quantities of the impurity 1-chlorobutadiene are produced. This is achieved by using a mixture of ethanol or methanol and water as the reaction medium. Such a reaction medium is a homogenous single-phase liquid, and the chloroprene cannot be recovered by distillation because of the formation of azeotropes with the methanol or ethanol and the specification specifies that temperatures below the boiling point of chloroprene are used. It is therefore necessary to add large quantities of water to cause the separation of a separate chloroprene liquid phase. This gives large quantities of a dilute aqueous solution of salt and alkanol, and this gives rise to considerable expense and difficulty in handling this aqueous phase and removing the methanol or ethanol from it. Furthermore the chloroprene phase will contain ethanol or methanol which is difficult to remove from the chloroprene. The British patent specification refers to U.S. Pat. No. 3,079,446 which discloses the use of mixtures of water and ether-alcohols, only to state that it require high temperatures of 80° C. to 120° C.

GB Pat. No. 1,218,869 discloses a process for the dehydrochlorination of inter alia 3,4-dichlorobutene-1 to chloroprene in the presence of various catalysts at temperatures in the range 40° C. to 70° C. Among catalysts listed are the ether-alcohols 2-methoxy ethanol, 2-methoxy ethanol and 1-methoxy-2-propanol. The specification refers to the use of up to 5% or even 10% by weight of catalyst based on weight of starting organic material, but it is clear that where catalysts are involved the minimum possible quantity will be used. The essential feature of the process of GB Pat. No. 1,218,869 is that the concentration of alkali metal hydroxide is initially at least 30% wt calculated on water and alkali metal hydroxide only and that it is used in sufficient excess to be able to react with all the halogen-containing compound present and still leave a final concentration of 25%. The specification states that in a continuous process the concentration should be maintained at at least 25% wt. FIG. 2 of the specification shows clearly the necessity for high concentrations of alkali metal hydroxide in water if low levels of 1-chloro-butadiene is to be achieved. However the use of such high concentrations of alkali metal hydroxide leads to considerable disadvantages. Thus because the final concentration of alkali metal hydroxide must be at least 25% wt., it is necessary to provide some means of recovering the alkali metal hydroxide for re-use. Furthermore at such very high concentrations of alkali metal hydroxide, the alkali metal chloride formed during the dehydrochlorination is likely to separate out during or after the reaction, so requiring frequent cleaning of the reactor and connecting pipes.

The production of chloroprene by the dehydrochlorination of 3,4-dichlorobutene is accompanied, as will be clear from a study of the patent specifications mentioned above, by various undesirable side reaction which reduce the yield of chloroprene and introduce undesirable impurities into the chloroprene. Two of these undesirable reactions are dimerisation and polymerisation. Another extremely undesirable side reaction is the production of 1-chlorobutadiene which is difficult to separate from chloroprene. The tendency of chloroprene to dimerise can be reduced by operating at low temperatures but this also reduces the rate at which chloroprene is produced and the problem of polymer formation can be minimised in other ways, for example by the use of polymerisation inhibitors. Furthermore if low temperatures are used the chloroprene cannot be removed from the reaction mixture as it is formed at atmospheric pressure. If the chloroprene is removed from the reaction mixture as a liquid it will be in contact with the reaction mixture at elevated temperatures for quite long periods of time, so giving the opportunity for further reactions.

A process for the dehydrochlorination of 3,4-dichlorobutene-1 has now been found which enables the amount of impurities to be reduced by comparison with processes operated at temperatures sufficient to distil the chloroprene from the reaction mixture as it is formed, which does not require the use of very high concentrations of alkali, which enables the chloroprene to be separated easily from the aqueous phase containing the alkali, and yet which surprisingly enables sufficiently high reaction rates to be obtained for the process to be commercially practicable.

According to the present invention the process for the production of chloroprene comprises continuously dehydrochlorinating 3,4-dichlorobutene-1 at a temperature in the range 40°–70° C. in a reaction medium which is a two phase liquid mixture of water and an alcohol in a volume ratio of water to alcohol from 90:10 to 5:95 in the presence of a standing concentration of not more than 10% by weight of alkali metal hydroxide in the aqueous phase, and separating an organic liquid phase containing chloroprene from the resulting mixture of aqueous and organic liquid phases.

The process of the present invention is carried out continuously. The reaction may be carried out in a stirred reaction vessel to which 3,4-dichlorobutene-1, water, alcohol and alkali metal hydroxide are fed continuously and from which liquid reaction mixture containing chloroprene is continuously withdrawn. A plurality of such stirred reactor vessels in series may be used, with the product from the first reactor in series overflowing into the next reactor.

The reaction temperature is preferably in the range 50°–70° C., for example 55°–65° C. Depending on the amount of reaction taking place in each reactor the temperature may rise adiabatically or may be controlled by cooling. The reaction is most conveniently carried out at atmospheric pressure and when using atmospheric pressure, temperatures much above 70° C. tend to cause a substantial amount of chloroprene to boil off from the reactor mixture. If the pressure is reduced much below atmospheric pressure the chloroprene may boil at the reaction temperature while the use of pressure much above atmospheric pressure involves additional expense in providing pressure resistant vessels and pumps for maintaining high pressures. In commercial plant it may be necessary to use a pressure somewhat above atmospheric pressure to overcome the back pressure of the distillation system used to recover the polychloroprene. It is therefore preferred to carry out the dehydrochlorination reaction at a pressure from 1 atmosphere to 1½ atmospheres absolute, for example at a pressure in the range 1 to 1¼ atmospheres absolute.

The reaction medium must consist of two liquid phases and the alcohol employed must be such as to give with the water two liquid phases under the reaction conditions used. Examples of suitable alcohols are higher alkoxyalkanols e.g. butoxyethanol, and higher alkanols e.g. these containing 3 to 5 carbon atoms e.g. propanol-1, propanol-2, butanol-1. The ability to form a separate liquid phase will depend on the nature of the alcohol, the relative quantities of alcohol and water, and the concentration of dichlorobutenes and chloroprene in the organic phase and of alkali metal hydroxide and alkali metal chloride in the aqueous phase, but for any given reaction mixture a suitable alcohol can be selected by simple test. Thus it is preferred to use an alcohol which, when shaken with a saturated brine solution containing 22% wt/wt NaOH at a volume ratio of alcohol to aqueous phase corresponding to that to be used in the dehydrochlorination process, forms a separate phase, which phase contains at least 0.1% wt/wt NaOH. An example of a volume ratio of alcohol to aqueous phase at which the test may be carried out is 3:1. It is particularly preferred to use alcohols which give a separate phase containing at least 0.5% wt/wt NaOH.

Thus when various alcohols were shaken with a saturated brine solution containing 22% wt/wt NaOH at a volume ratio of alcohol to aqueous phase 3:1, the values obtained for the NaOH content of the alcohol phase (at room temperature) were:

| Alcohol | NaOH Contentl |
| --- | --- |
| sec-butanol (butanol-2) | 0.05% wt/wt |
| iso-butanol (trimethyl methanol) | 0.19% wt/wt |
| n-butanol (butanol-1) | 0.6% wt/wt |
| 2-butoxyethanol | 3.6% wt/wt |

It will be seen that butanol-2 is not a preferred solvent, while n-butanol and 2-butoxyethanol are preferred solvents. It is particularly preferred to use 2-butoxyethanol.

It is preferred to use less than 50 volumes of water for every 50 volumes of alcohol, more preferable to use a water:alcohol volume ratio of from 40:60 to 10:90.

The process of the present invention is a continuous process and therefore requires both alkali metal hydroxide and 3,4-dichlorobutene-1 to be fed continuously into the reaction medium. The alkali metal hydroxide, preferably sodium hydroxide, is most conveniently fed as an aqueous solution. This aqueous solution may have a concentration of 25% wt/wt sodium hydroxide, or more, but the process is so operated that the standing concentration in the aqueous phase in the reaction medium does not exceed 10% by wt based on wt of aqueous phase. This minimises the risk of precipitation of alkali metal chloride from the reaction medium.

The concentration of the alkali metal hydroxide in the aqueous phase from the dehydrochlorination reaction preferably does not exceed 4% by wt, more preferably 3% by wt, based on wt of aqueous phase. A low concentration of alkali metal hydroxide in the aqueous phase enables the aqueous phase to be discarded without the necessity of providing a means for recovering and recycling the alkali metal hydroxide. In order to obtain such a low concentration of alkali metal hydroxide in the aqueous effluent from the reaction, it will usually be desirable to employ at least two reactors in series so that the necessary low concentration of alkali metal hydroxide can be maintained in the final reactor.

The 3,4-dichlorobutene-1 and the alkali metal hydroxide are fed to the reaction at a molar ratio of alkali metal hydroxide to 3,4-dichlorobutene-1 which is preferably not more than 1.3:1, more preferably not more than 1.2:1. In order for the reaction to proceed satisfactory it will however usually be necessary to have a stoichiometric excess of alkali metal hydroxide.

The rate at which the 3,4-dichlorobutene-1 is fed to the dehydrochlorination reaction is preferably controlled to give a residence time in the reaction system in the range 10 to 60 minutes.

The rate at which 3,4-dichlorobutene-1 is fed to the reaction is preferably such as to maintain a 3,4-dichlorobutene-1 concentration in the reactor to which it is fed in the range 2 to 15% wt/wt.

The dehydrochlorination is preferably carried out in the presence of a polymerisation inhibiton for example nitric oxide and the sodium hydroxide may contain sodium sulphide.

The chloroprene is recovered from the dehydrochlorination as a liquid. The chloroprene will be contained in the separate alcohol phase, and the total effluent from the dehydrochlorination reaction may be fed to a decanter from which the organic phase containing the alcohol, chloroprene, and any unreacted 3,4-dichlorobutene is separated. This organic phase may then be subjected to distillation to recover chloroprene. It is an advantage of the use of 2-butoxyethanol as the alcohol that chloroprene can be readily separated from it by distillation in a high state of purity. It may be desirable to discard some of the alcohol and to replace it by fresh alcohol to prevent undesirable higher boiling materials accumulating in the alcohol.

The aqueous phase recovered from the decanter will contain alkali metal chloride, and some residual alkali metal hydroxide. It may also contain some alcohol, which may be recovered by distillation and recycled.

The invention will now be illustrated by reference to the accompanying drawing which is a diagrammatic representation of the apparatus used.

The apparatus comprises first and second reactors 1 and 2, each provided with a heating/cooling jacket 3 whose temperature is controlled by a temperature controller 4, and agitator 5, and a reflux condenser 6. Pipes 7, 8 and 9 are provided leading into reactor 1 through which a mixture of nitrogen and nitric oxide, liquid 3,4-dichlorobutene-1 and aqueous sodium hydroxide solution respectively may be fed.

Reactor 1 is provided with an internal stand pipe 10 open at the top through which any liquid in reactor 1 overflows when the liquid level in the reactor reaches the top of the pipe. Stand pipe 10 is connected to a device 11 by means of which gas coming from the head of the reflux condenser 6 attached to reactor 1 may be mixed with the liquid overflowing from reactor 1 and passed together to reactor 2. Reactor 2 is also provided with a open-topped stand pipe 12, through which liquid in reactor 2 will overflow into separator 13. Separator 13 is designed to separate liquid fed to it through stand pipe 12 into a heavy liquid phase which can be discharged through pipe 14 in the base of the separator and a lighter liquid layer which can be removed through pipe 15 in the side of the separator, to a fractionating column 16. Separator 13 has a gas space which is connected by way of reflux condenser 6 to reactor 2. The column 16 has 15 sieve trays and the pipe 15 is connected at the fifth tray from the base. A pipe 17 is provided near the base of the column for introducing a mixture of nitrogen and nitric oxide to inhibit polymerisation within the column. The level of liquid within column 16 is controlled by a level controller 18 which controls a valve 19 through which liquid can be removed from the column reboiler. This liquid after passing through a cooler 20 is pumped through pump 21 back to reactor 1. Pipe 22 enables fresh alcohol to be introduced into the pipe 23 leading to reactor 1. Liquid can also be withdrawn from the base of the column through pipe 24 by opening valve 25.

Temperature controller 26 controls the temperature of reboiler 30 which is fitted with a pipe 31 through which steam can be introduced into the reboiler if desired.

Vapours from the head of column 16 are passed to a condenser 27 and part of the liquid condensate is returned to column 16 as reflux and the remainder recovered after passing through cooler 28. Any uncondensed materials were discharged through pipe 29.

In operation a mixture of nitrogen and nitric oxide (polymerisation inhibitor) 3,4-dichlorobutene-1, and caustic soda solution, for example up to 25% wt/wt aqueous solution, are fed through pipes 7, 8 and 9 into reactor 1, together with e.g. 2-butoxyethanol, fed in through pipe 23. The contents of the reactor are maintained at the desired reaction temperature and agitated and reaction product overflows into reactor 2 through pipe 10 together with the nitrogen/nitric oxide mixture from the head of condenser 6.

The liquid overflow from reactor 2 is separated into an aqueous lower layer discharged through pipe 14 and an organic layer which is fed to column 16 which is operated to distil off pure chloroprene overhead, leaving liquid 2-butoxyethanol in the base which is recycled to reactor 1 through pipe 23. Nitrogen/nitric oxide mixture originally fed to reactor 1 passes through reactor 2 and then from reactor 2 through reflux condenser 6 to separator 13. Nitrogen/nitric oxide mixture is also introduced into distillation column 16.

If high boiling materials accumulate in the 2-butoxyethanol a bleed may be taken through valve 25 and fresh 2-butoxyethanol may be added through pipe 22.

The brine removed from separator 13 through pipe 14 may be distilled to recover dissolved 2-butoxyethanol.

EXAMPLE 1

Apparatus as described above was used. 99.4% 3,4-dichlorobutene-1 (245 ml/hr) (2.24 moles 3,4-dichlorobutene-1), 20% (wt/wt) aqueous sodium hydroxide (453 ml/hr) containing 0.05% sodium sulphide were pumped into reactor 1. Reactors 1 and 2 each had a capacity of 1000 ml when full to the top of the overflow pipe and each initially contained 500 ml of a 75/25 volume/volume mixture of 2-butoxyethanol and 20% wt/wt aqueous sodium hydroxide solution. The temperature of reactors 1 and 2 was maintained at 70° C., and the pressure in the reactors was maintained at atmospheric pressures.

The composition of the aqueous phase leaving reactor 1 after a steady state had been reached was about 4.5% NaOH and 19% wt/wt NaCl. The organic phase contained approximately 16% wt/wt chloroprene and 9% wt/wt 3,4-dichlorobutene-1.

The composition of the aqueous phase leaving the second reactor after a steady state had been reached was about 2% wt/wt NaOH and 22% wt/wt Na Cl. The organic phase which contained about 17.3% wt/wt chloroprene and 6.3% wt/wt unchanged 3,4-dichlorobutene-1, the remainder being 2-butoxyethanol, was fed to still 16 which was operated at a bottom temperature of 109° C. and at atmospheric pressure. The reflux/distillate ratio was controlled by a magnetic still head of a type well-known to those skilled in the art, and was set at 4:1, so as to give an overhead product containing 99.5% chloroprene, and only 0.5% 1-chlorobutadiene and 0.01–0.02% acetaldehyde, and a base product of 2-butoxyethanol containing only 0.5% chloroprene. The base product was continuously recycled to the first reactor.

Chloroprene was produced at the rate of 2.19 g mole/hr/liter total reaction volume.

EXAMPLE 2

An experiment was carried out under the same conditions as Example 1 but with both reactors maintained at a temperature of 60° C. Chloroprene was produced at a rate of 2.0 g mole/hr/liter total reaction volume, and contained only 0.2% wt/wt of -chlorobutadiene.

The waste brine discharged from separator 13 through pipe 14 was distilled to remove 2-butoxyethanol. After a distillate equivalent to 7% wt/wt of the brine had been taken off, the residue contained 80 ppm of 2-butoxyethanol and 95 ppm of total organic carbon.

The residence time in the above examples was about 17 minutes. Residence time in minutes as used in this specification is calculated by dividing the total volume of reaction mixture in the reactors by the total volume of organic and aqueous material fed to the reactor per minute, including fresh 3,4-dichlorobutene-1 and sodium hydroxide solution, and recycled 2-butoxyethanol and 3,4-dichlorobutene-1.

EXAMPLE 3

The apparatus described above was used. With volumes of 750 ml and 500 ml and temperatures of 64° and 70° in the first and second reactors respectively, 3,4-dichlorobutene-1 was fed at a rate of 225 g/h and 20% w/w sodium hydroxide at 432 g/h. The organic phase from the second reactor was fed to the distillation column in which steam (140 g/h) was fed to the reboiler giving a column base temperature of 102° and a stripped product containing 0.1% chloroprene. Chloroprene was obtained overhead in 98% molar yield, and contained only 0.5% 1-chlorobutadiene and 0.03% acetaldehyde.

Under equilibrium conditions the reactors contained approximately 75% w/w of organic phase which contained 5.9% w/w and 3.6% w/w dichlorobutene in the first and second reactors respectively. The corresponding sodium hydroxide concentrations in the aqueous phase were 4.1% w/w and 2.3% w/w, and the residence times approximately 20 and 13 minutes.

We claim:

1. The process for the production of chloroprene which comprises continuously dehydrchlorinating 3,4-dichlorobutene-1 at a temperature in the range of 40°–70° C. in a reaction medium which is a two phase liquid mixture of water and an alcohol which when shaken with a saturated brine solution containing 22% wt/wt NaOH at a volume ratio of alcohol to aqueous phase corresponding to that to be used in the dehydrochlorination process gives a separate phase containing at least 0.5% wt/wt NaOH, said water and alcohol being in a volume ratio of water to alcohol of 90:10 to 5:95 in the presence of a standing concentration of not more than 10% by weight of alkali metal hydroxide in the aqueous phase, recovering the chloroprene from the dehydrochlorination zone as a liquid by removing the resulting mixture of aqueous and organic liquid phases from the reactor, separating an organic liquid phase containing chloroprene from the resulting mixture of aqueous and organic liquid phases, and then distilling chloroprene from said organic liquid phase.

2. A process according to claim 1 wherein the reaction is carried out in two reactors in series.

3. A process according to claim 1 wherein the reaction temperature is in the range 50°–70° C.

4. A process according to claim 3 wherein the reaction temperature is in the range 55°–65° C.

5. A process according to claim 1 wherein the process is carried out at a temperature of from 1 to 1½ atmospheres absolute.

6. A process according to claim 5 wherein the process is carried out at a pressure in the range 1 to 1¼ atmospheres absolute.

7. A process according to claim 1 wherein the alcohol is n-butanol or 2-butoxyethanol.

8. A process according to claim 1 wherein the reaction medium contains less than 50 volumes of water for every 50 volumes of alcohol.

9. A process according to claim 8 wherein the water to alcohol volume ratio in the reaction medium is from 40:60 to 10:90.

10. A process according to claim 3 wherein the concentration of the aqueous phase recovered from the dehydrochlorination reaction is not greater than 4% by weight, based on weight of aqueous phase.

11. A process according to claim 3 wherein the 3,4-dichlorobutene-1 and the alkali metal hydroxide are fed to the reaction at a molar ratio of alkali metal hydroxide of 3,4-dichlorobutene-1 which is not more than 1.3:1.

12. A process according to claim 11 wherein there is a stoichiometric excess of alkali metal hydroxide.

13. A process according to claim 3 wherein the rate at which the 3,4-dichlorobutene as fed to a reactor is such as to maintain a 3,4-dichlorobutene-1 concentration in that reactor in the range 2 to 15% wt/wt to total contents.

* * * * *

UNITED STATES PATENT AND TRADEMARK OFFICE
CERTIFICATE OF CORRECTION

PATENT NO. : 4,308,410
DATED : December 29, 1981
INVENTOR(S) : ANTONY H.P. HALL and JEAN P. MERLE It is certified that error appears in the above-identified patent and that said Letters Patent are hereby corrected as shown below:

Col. 1, line 4, after "Ser. No.", delete "469,697" and insert --769,697-- in lieu thereof.

Col. 7, line 2, after "of" and before "-" insert --1--.

Signed and Sealed this

Second Day of November 1982

[SEAL]

Attest:

GERALD J. MOSSINGHOFF

Attesting Officer

Commissioner of Patents and Trademarks